United States Patent [19]

Correa et al.

[11] Patent Number: 5,290,957
[45] Date of Patent: Mar. 1, 1994

[54] PROCESS FOR THE STEREOSELECTIVE PREPARATION OF PHENYLISOSERINE DERIVATIVES USED IN MAKING TAXOLS

[75] Inventors: Arlene Correa, Sao Carlos, Brazil; Jean-Noel Denis; Andrew-Elliot Greene, both of Uriage, France

[73] Assignee: Rhone Poulenc Rorer S.A., France

[21] Appl. No.: 949,548

[22] PCT Filed: May 21, 1991

[86] PCT No.: PCT/FR91/00406
§ 371 Date: Nov. 20, 1992
§ 102(e) Date: Nov. 20, 1992

[87] PCT Pub. No.: WO91/17977
PCT Pub. Date: Nov. 28, 1991

[30] Foreign Application Priority Data

May 22, 1990 [FR] France ............................... 90 06368

[51] Int. Cl.⁵ ................. C07D 305/14; C07C 229/36; C07C 271/22
[52] U.S. Cl. ..................................... 549/510; 560/29; 562/418; 562/444
[58] Field of Search ......................... 549/510; 560/29; 562/418, 444

[56] References Cited

FOREIGN PATENT DOCUMENTS

253738  1/1988  European Pat. Off. .
336941 10/1989  European Pat. Off. .
414610  2/1991  European Pat. Off. .

OTHER PUBLICATIONS

Jour. of Org. Chem, vol. 51, No. 1, 1986 Denis, et al. "An Efficient, Enantioselective Synthesis of the Taxol Side Chain", pp. 46–50.
Jour. of the Amer. Chem. Soc., vol. 110, No. 17, Aug. 17, 1988, Denis, et al, "A Highly Efficient, Practical Approach to Natural Taxol", pp. 5917–5919.
Archiv der Pharmazie, vol. 308, 1975, Kamandi, et al. "Die Synthese von Ammonolyse von Beta-Phenyl-Glycidestern, II", pp. 135–141.

Primary Examiner—Bernard Dentz
Attorney, Agent, or Firm—Morgan & Finnegan

[57] ABSTRACT

A stereoselective process for preparing phenylisoserine derivatives is disclosed. Benzylamine is reacted with an agent for introducing a phenyl or a t-butoxycarbonyl group. The product undergoes double anionization and then is reacted with acrolein to provide a mixture of alcohol syn and anti diasteroisomers. The syn isomer is isolated by chromatography. Whereupon, the hydroxyl is protected and the product is oxidized to provide the phenylisoserine derivative.

10 Claims, No Drawings

PROCESS FOR THE STEREOSELECTIVE PREPARATION OF PHENYLISOSERINE DERIVATIVES USED IN MAKING TAXOLS

FIELD OF THE INVENTION

The present invention relates to a process for the stereoselective preparation of phenylisoserine derivatives of the general formula

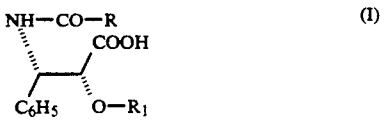

in which R is a phenyl radical or a tert-butoxy radical and $R_1$ is a protecting group for the hydroxyl group.

DESCRIPTION OF THE INVENTION

In general formula (I), $R_1$ is more particularly a methoxymethyl, 1-ethoxyethyl, benzyloxymethyl, (β-trimethylsilylethoxy)methyl, tetrahydropyranyl or 2,2,2-trichloroethoxycarbonyl radical. The radical $R_1$ is preferably the 1-ethoxyethyl radical.

The procedure of general formula (I) are useful for preparing the baccatin III and 10-deacetylbaccatin III derivatives of the general formula

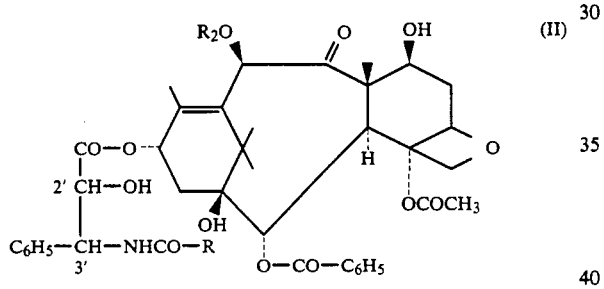

in which R is a phenyl radical or a tert-butoxy radical and $R_2$ is a hydrogen atom or an acetyl radical.

The products of general formula (II) in which R is a phenyl radical correspond to taxol and 10-deacetyltaxol and the products of general formula (II) in which R is a tert-butoxy radical correspond to those described in European patent 253 738.

The products of general formula (II), and in particular the product of general formula (II) in which $R_2$ is a hydrogen atom and which is in the 2'R,3'S form, have particularly valuable antitumoral and antileukaemic properties.

The products of general formula (II) can be obtained by reacting a product of general formula (I) with a taxane derivative of the general formula

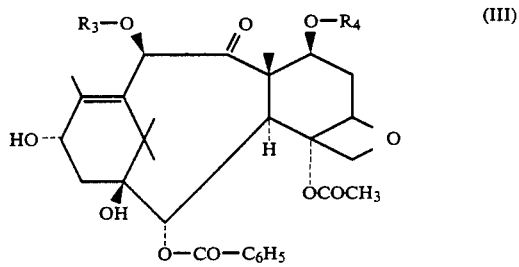

in which $R_3$ is an acetyl radical or a protecting group for the hydroxyl group and $R_4$ is a protecting group for the hydroxyl group, and then replacing the protecting groups $R_1$ and $R_4$ and, if appropriate, $R_3$ with a hydrogen atom under the conditions described by J-N. DENIS et al., J. Amer. Chem. Soc., 110(17) 5917–5919 (1988).

It is possible to react the racemic product of general formula (I) and subsequently to separate the diastereoisomers of the product of general formula (II), or else to react each of the enantiomers of the product of general formula (I) separately with the product of general formula (III).

According to the present invention, the acid of general formula (I) (syn form, racemic mixture) can be obtained from benzylamine.

By reaction with an agent for introducing a benzoyl or t-butoxycarbonyl group, benzylamine is converted to a product of the general formula

in which R is as defined above, which, after double anionisation, is reacted with acrolein to give the alcohol of the general formula

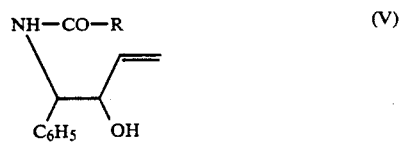

in which R is as defined above, in the form of a syn and anti mixture containing essentially the syn form:

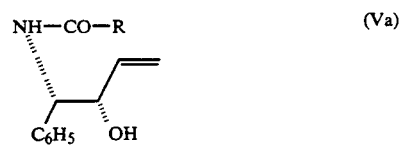

The alcohol of general formula (Va), previously separated from the mixture of the syn and anti forms, is oxidized to the acid of general formula (I) after protection of the hydroxyl group.

The product of general formula (IV) is generally obtained by reaction with an agent for introducing a benzoyl or t-butoxycarbonyl group, preferably benzoyl chloride or di-t-butyl dicarbonate, as the case may be. The reaction is generally carried out in an organic solvent such as methylene chloride, in the presence of an inorganic base such as sodium hydroxide or sodium bicarbonate or carbonate, or an organic base such as triethylamine or 4-dimethylaminopyridine, at a temperature of between 0° and 50° C.

The double anionization of the product of general formula (IV) is generally carried out using equivalents of an organolithium derivative such as s-butyllithium, in an anhydrous organic solvent such as tetrahydrofuran, at a temperature below −50° C. and preferably of about −78° C.

The reaction of acrolein with the dianion of the product of formula (IV) is generally carried out by adding acrolein, preferably freshly distilled, to the solution of the dianion, previously cooled to about 100° C. After hydrolysis, the product of general formula (V) is obtained in the form of a mixture of the syn and anti diastereoisomers, from which the syn form of formula (Va) is separated by chromatography.

Protection of the hydroxyl group of the alcohol of general formula (Va) is effected under the normal conditions for the preparation of ethers and acetals, for example in accordance with the processes described by J-N. DENIS et al., J. Org. Chem., 51, 46–50 (1986).

Oxidation of the protected alcohol of general formula (Va) is preferably carried out by means of an alkali metal periodate (sodium periodate), in the presence of a catalytic amount of a ruthenium salt ($RuCl_2$) and sodium bicarbonate, in an aqueous-organic medium such as, for example, a carbon tetrachloride/acetonitrile/water mixture. The reaction is generally carried out at a temperature of about 20° C.

Oxidation can also be carried out by means of potassium permanganate, for example in the presence of adogen in a pentane/water mixture, or in the presence of aliquat or dicyclohexyl-18 crown-6 in methylene chloride or in a pyridine/water mixture. It is also possible to use triethylbenzylammonium permanganate in the presence of pyridine in methylene chloride.

The product of general formula (I) (syn form, racemic mixture) can be resolved into its enantiomers, and in particular into its 2R,3S enantiomer, for example in accordance with the process described by D. Petterson, Thesis at the University of Lund (Sweden), pages 27–28 (1989).

EXAMPLES

The following Examples, which are given without implying a limitation, show how the invention can be put into practice.

EXAMPLE 1

218.5 µl (214.3 mg, 2 mmol) of benzylamine and 10 $cm^3$ of dry methylene chloride are introduced under argon into a 50 $cm^3$ single-necked flask surmounted by a condenser and equipped with a magnetic stirring system. 418 µl (303 mg, 3 mmol) of triethylamine and, in small portions (exothermic reaction), 524 mg (2.4 mmol) of pure di-t-butyl dicarbonate are added to the solution obtained. When the addition is complete, the reaction is left to proceed for 4 hours at a temperature of about 20° C. and the resulting reaction mixture is then diluted with 40 $cm^3$ of methylene chloride. The organic phase is washed 4 times with 5 $cm^3$ of water and once with 5 $cm^3$ of a saturated aqueous solution of sodium chloride. The organic phase is dried over anhydrous sodium sulphate. After filtration, the methylene chloride is driven off under reduced pressure on a rotary evaporator. The residue obtained (505 mg) is purified by chromatography on a column of silica gel using an ethyl acetate/methylene chloride mixture (5/95 by volume) as the eluent. 406 mg (1.96 mmol) of t-butyl benzylcarbamate are thus obtained in the form of a white solid with a yield of 98%, said product having the following characteristics:

melting point: 55.5°–56.5° C. (hexane)

infrared spectrum (film): characteristic absorption bands at 3350, 3315, 3080, 3060, 3040, 3010, 2980, 2960, 2930, 1680, 1550, 1450, 1442, 1395, 1370, 1315, 1290, 1255, 1180, 1140, 1080, 1055, 1035, 950, 930, 918, 865, 770, 750, 725 and 700 $cm^{-1}$ proton nuclear magnetic resonance spectrum (300 MHz; $CDCl_3$; chemical shifts in ppm; coupling constants J in Hz) 1.46 (s, 9H); 4.3 (d, J=5.7, 2H); 4.84 (s broad, 1H); 7.22–7.34 (m, 5H)

$^{13}C$ nuclear magnetic resonance spectrum ($CDCl_3$): 28.38 ($CH_3$); 44.69 ($CH_2$); 79.43 (C); 127.27 (CH); 127.41 (CH); 128.54 (CH); 138.93 (C); 155.84 (C)

EXAMPLE 2

4.2 g (20.3 mmol) of t-butyl benzylcarbamate, 40 $cm^3$ of anhydrous tetrahydrofuran and 6.5 $cm^3$ (5.0 g, 43 mmol) of tetramethylethylenediamine (TMEDA) are introduced successively into a 250 $cm^3$ single-necked flask placed under argon and equipped with a magnetic stirring system. The solution obtained is cooled to 78° C. and 60 $cm^3$ (60 mmol) of a 1M solution of secondary butyllithium in hexane are then added dropwise. The reaction is left to proceed for 3 hours at this temperature and the mixture is then cooled to $-100°$ C. 3 $cm^3$ (2.5 g, 44.9 mmol) of freshly distilled acrolein are then added and the reaction is left to proceed for 3 to 4 minutes at this temperature and then for 1 hour at $-78°$ C. The resulting reaction mixture is hydrolyzed at $-78°$ C. with 20 $cm^3$ of water and then extracted with 2 times 30 $cm^3$ of ether. The organic phases are combined and then washed twice with 20 $cm^3$ of water and once with 10 $cm^3$ of a saturated aqueous solution of sodium chloride. They are then dried over anhydrous sodium sulphate. After filtration, the solvents are driven off under reduced pressure. The residue obtained (11.6 g) is purified on a column of silica gel using a methylene chloride/ether mixture (95/5 by volume) as the eluent. 2.606 g (9.91 mmol) of 1-phenyl-1-t-butoxycarbonylamino-2-hydroxybut-3-ene are obtained with a yield of 49% in the form of a mixture of the syn and anti diastereoisomers in a ratio of 6/1.

The syn diastereoisomer is separated from the anti diastereoisomer by chromatography on a column of silica gel using an ether/hexane/methylene chloride mixture (5/45/50 by volume) as the eluent.

The syn diastereoisomer has the following characteristics:

melting point: 86.5°–88° C. (hexane)

infrared spectrum (film): characteristic absorption bands at 3400, 2975, 2920, 1690, 1500, 1450, 1390, 1365, 1250, 1175, 1080, 1050, 1020, 995, 920, 755 and 700 $cm^{-1}$ proton nuclear magnetic resonance spectrum (300 MHz; $CDCl_3$; chemical shifts in ppm; coupling constants J in Hz): 1.40 (s, 9H); 1.9 (s broad, 1H); 4.38 (pst, J=4.6 and 4.8, 1H); 4.70 (s broad, 1H); 5.20 (dt, J=1.4 and 10.5, 1H); 5.26 (s broad, 1H); 5.34 (dt, J=1.4 and 17.2, 1H); 5.86 (ddd, J=54, 10.5 and 17.2, 1H); 7.24–7.37 (m, 5H)

$^{13}C$ nuclear magnetic resonance spectrum ($CDCl_3$) 28.12 ($CH_3$); 58.74 (CH); 75.33 (CH); 79.58 (C); 116.36 ($CH_2$); 126.69 (CH); 127.26 (CH); 128.32 (CH); 137.17 (CH); 139.96 (C); 155.89 (C)

mass spectrum (c.i.) ($NH_3$+isobutane): 321 ($M^+$+isobutane); 281 ($MH^+$+$NH_3$); 264 ($MH^+$, parent peak); 246, 225, 208, 190, 164, 124, 106 elemental analysis:

calculated % C 68.41 H 8.04 N 5.32 measured % C 68.15 H 7.98 N 5.34

The anti diastereoisomer has the following characteristics:

infrared spectrum (film): characteristic absorption bands at 3370, 3060, 2975, 2920, 1680, 1530, 1470, 1290, 1250, 1170, 1040, 1000, 930, 900, 870, 840, 755 and 700 cm$^{-1}$ proton nuclear magnetic resonance spectrum (300 MHz; CDCl$_3$; chemical shifts in ppm; coupling constants J in H$_2$): 1.41 (s, 9H); 1.8 (s broad, 1H); 4.43 (psq, J=0.9 and 4.4, 1H); 4.78 (s broad, 1H); 5.18 (dt, J=1.2 and 10.5, 1H); 5.24 (s broad, 1H); 5.26 (dt, J=1.2 and 17, 1H); 5.71 (ddd, J=5.5, 10.5 and 17, 1H); 7.24–7.36 (m, 5H)

$^{13}$C nuclear magnetic resonance spectrum (CDCl$_3$): 28.23 (CH$_3$); 59.22 (CH); 75.33 (CH); 79.85 (C); 117.06 (CH$_2$); 127.29 (CH); 127.56 (CH); 128.33 (CH); 136.27 (CH); 138.14 (C); 155.61 (C)

elemental analysis:
calculated % C 68.41 H 8.04 N 5.32
measured % C 68.43 H 8.14 N 5.08

EXAMPLE 3

526 mg (2.0 mmol) of 1-phenyl-1-t-butoxycarbonylamino-2-hydroxybut-3-ene, syn form, 20 cm$^3$ of dry methylene chloride, 1.9 cm$^3$ (20.0 mmol) of distilled ethyl vinyl ether and 50.2 mg (0.2 mmol) of pyridinium p-toluenesulphonate (PPTS) are introduced successively into a 50 cm$^3$ single-necked flask placed under an argon atmosphere and equipped with a magnetic stirring system. The resulting homogeneous reaction mixture is left to react for 4.5 hours at a temperature of about 20° C. When the reaction is complete, 1 drop of pyridine is added and the reaction mixture is then diluted in 60 cm$^3$ of methylene chloride. The organic phase is washed twice with water and twice with a saturated aqueous solution of sodium chloride and then dried over anhydrous sodium sulphate. After filtration, the solvents are driven off under reduced pressure on a rotary evaporator. The residue obtained is purified by passage over a column of silica gel using a hexane/ether mixture (8/2 by volume) as the eluent. 580 mg (1.73 mmol) of 1-phenyl-1-t-butoxycarbonylamino-2-(1-ethoxyethoxy)but-3-ene are obtained with a yield of 87% in the form of two epimers in a ratio of 55/45, said product having the following characteristics:

melting point: 66°–72° C.

infrared spectrum (film): characteristic absorption bands at 3370, 2970, 2925, 2875, 1680, 1520, 1495, 1365, 1285, 1250, 1170, 1080, 1050, 1005, 955, 930, 890, 870, 755 and 705 cm$^{-1}$ proton nuclear magnetic resonance spectrum (300 MHz; CDCl$_3$; chemical shifts in ppm; coupling constants J in Hz): 0.9 (min) and 1.07 (maj) (2t, J=7, 3H); 1.05 (min) and 1.22 (maj) (2d, J=5.3 (min) and 5.4 (maj), 3H); 1.40 (s, 9H); 2.90–2.98 and 3.05–3.51 (m, 2H); 4.16 and 4.23 (2psdd, J=6.6 and 7, 1H); 4.31 (min) and 4.62 (maj) (2q, J=5.3 (min) and 5.4 (maj), 1H); 4.71 (maj) and 4.73 (min) (2m, 1H); 5.22 and 5.23 (2dt, J=1.2 and 10.5, 1H); 5.25 and 5.30 (2dt, J=1.2 and 17.4, 1H); 5.37 and 5.44 (2m, 1H); 5.77 (min) and 5.91 (maj) (2ddd, J=7, 10.5 and 17.4, 1H); 7.17–7.37 (m, 5H)

elemental analysis:
calculated % C 68.03 H 8.71 N 4.18
measured % C 68.00 H 8.78 N 4.13

EXAMPLE 4

A solution of 251 mg (0.75 mmol) of 1-phenyl-1-t-butoxycarbonylamino-2-(1-ethoxyethoxy)but-3-ene, syn form, in 1.5 cm$^3$ of acetonitrile is introduced into a 15 cm$^3$ single-necked flask placed under an argon atmosphere and equipped with a magnetic stirring system. 1.5 cm$^3$ of carbon tetrachloride, 2.25 cm$^3$ of distilled water and, with thorough stirring, 409.5 mg (4.875 mmol) of sodium bicarbonate are then added successively. 882 mg (4.125 mmol) of sodium periodate are then added in small portions. The reaction medium is left to react for 5 minutes, with stirring (evolution of gas), and 25.1 mg (10% by weight) of RuCl$_3$ are then added all at once. The reaction mixture, which has turned black and become highly heterogeneous, is left to react for 48 hours at a temperature of about 20° C., with vigorous stirring.

The reaction mixture is diluted with water to give a total volume of 12 cm$^3$. The black basic aqueous phase is extracted 3 times with 20 cm$^3$ of ether. The basic phase is then cooled to 0° C., after which it is treated dropwise with 3 cm$^3$ of a 2M aqueous solution of hydrochloric acid, in the presence of 30 cm$^3$ of methylene chloride, with vigorous stirring. The resulting acidic aqueous phase is extracted 8 times with 35 cm$^3$ of methyl chloride. The organic phases are combined and washed with 3 times 8 cm$^3$ of water and 1 times 10 cm$^3$ of a saturated aqueous solution of sodium chloride. They are dried over a 1/1 (w/w) mixture of sodium sulphate and magnesium sulphate and filtered under reduced pressure on Celite. The solvents are driven off under reduced pressure to a volume of 5 to 8 cm$^3$. The residue is dried over a 4 molecular sieve. The organic phase is separated from the molecular sieve and the remaining solvent is then driven off on a rotary evaporator.

205 mg (0.58 mmol) of pure 3-phenyl-3-t-butoxycarbonylamino-2-(1-ethoxyethoxy)propionic acid, syn form, are obtained with a yield of 77% in the form of a pale yellow oil having the following characteristics:

infrared spectrum (film): characteristic absorption bands at 3700–2200, 3060, 2980, 2930, 2850, 1720, 1660, 1602, 1590, 1500, 1450, 1400, 1370, 1280, 1250, 1170, 1080, 1050, 1030, 955, 930, 890 and 700 cm$^{-1}$ proton nuclear magnetic resonance spectrum (300 MHz; CDCl$_3$; chemical shifts in ppm; coupling constants J in Hz); 0.81 and 1.04 (2t, J=7, 3H); 1.18 and 1.20 (2d, J=5.4, 3H); 1.42 (s, 9H); 2.60–2.88 and 3.15–3.52 (m, 2H); 4.35–4.50 and 4.65–4.80 (m, 2H); 5.29 (s broad, 1H); 5.72 (s broad, 1H); 7.13–7.38 (m, 5H); 8.52 (s broad, 1H).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:
1. Process for the stereoselective preparation of phenylisoserine derivatives of formula

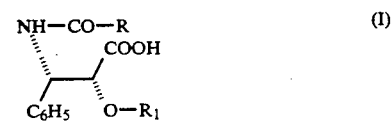

in which R is a phenyl or tert-butoxy radical and R$_1$ is a protecting group for the hydroxyl group, comprising treating benzylamine with an agent for introducing a benzoyl or t-butoxycarbonyl group to give the product of formula

which, after double anionization, is reacted with acrolein to give the alcohol of formula

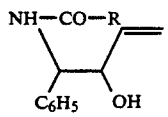

in the form of a syn and anti mixture, from which the syn form:

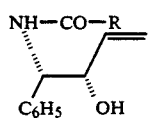

is separated, the hydroxyl group of said syn form is protected and the alcohol protected in this way is then oxidized to give the phenylisoserine derivative of formula (I) in the syn form, which is optionally separated into enantiomers.

2. Process according to claim 1, wherein the agent for introducing the benzoyl or t-butoxycarbonyl group is benzoyl chloride or di-t-butyl dicarbonate, which is reacted with benzylamine in an inert organic solvent, in the presence of an inorganic base, or an organic base.

3. Process according to claim 1, wherein acrolein is reacted with N-benzylbenzamide or t-butyl benzylcarbamate, previously anionized by reaction with 2 equivalents of an organolithium derivative, in an inert organic solvent, at a temperature of about −100° C.

4. Process according to claim 1, wherein the hydroxyl group of the alcohol is protected in accordance with known methods and the protected alcohol is then oxidized by means of an oxidizing agent selected from sodium periodate in the presence of a catalytic amount of a ruthenium derivative, or potassium permanganate.

5. Process for the preparation of baccatin III and 10-deacetylbaccatin III derivatives of formula

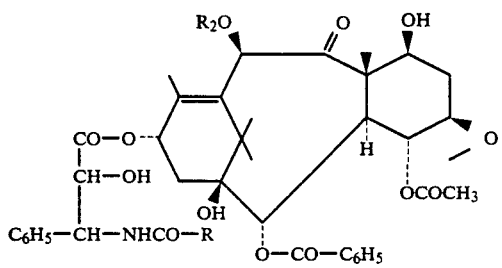

in which R is a phenyl radical or a tert-butoxy radical and $R_2$ is a hydrogen atom or an acetyl radical, comprising treating benzylamine with an agent for introducing a benzoyl or t-butoxycarbonyl group, to obtain the product of formula

which, after double anionization, is reacted with acrolein to give the alcohol of the formula

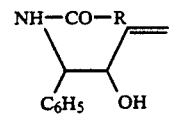

in the form of a syn and anti mixture, from which the syn form:

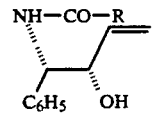

is separated, the hydroxyl group of said syn form is protected and the alcohol protected in this way is then oxidized to give the phenylisoserine derivative of formula:

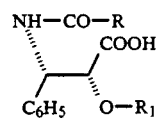

in which $R_1$ is a protecting group for the hydroxyl group, in the syn form, the enantiomers of which are optionally separated, and which is reacted with a taxane derivative of formula

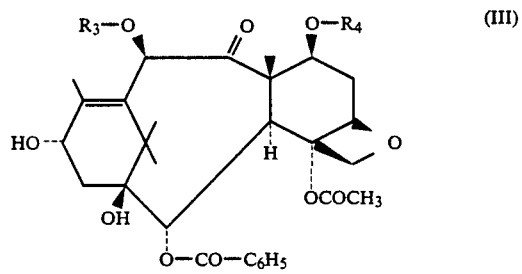

in which $R_3$ is an acetyl radical or a protecting group for the hydroxyl group and $R_4$ is a protecting group for the hydroxyl group, and then the product of formula (II) is isolated after replacing the protecting groups $R_1$ and $R_4$ with hydrogen atoms and optionally replacing $R_3$ with a hydrogen atom.

6. Process according to claim 2, wherein the inorganic base is sodium hydroxide or sodium bicarbonate or carbonate.

7. Process according to claim 2 wherein the organic base is triethylamine or 4-dimethylaminopyridine.

8. Process according to claim 3, wherein the organolithium derivative is s-butyllithium.

9. Process according to claim 3, wherein the inert organic solvent is tetrahydrofuran.

10. Process according to claim 2, wherein the organic solvent is methylene chloride.

* * * * *